US00PP17649P3

(12) United States Plant Patent
Drewlow

(10) Patent No.: US PP17,649 P3
(45) Date of Patent: Apr. 24, 2007

(54) **NEW GUINEA *IMPATIENS* PLANT NAMED 'APPLAUSE WHITE'**

(50) Latin Name: *Impatiens hawkeri*
Varietal Denomination: Applause White

(75) Inventor: Lyndon W. Drewlow, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/209,361

(22) Filed: Aug. 23, 2005

(65) Prior Publication Data

US 2006/0041976 P1 Feb. 23, 2006

Related U.S. Application Data

(60) Provisional application No. 60/603,770, filed on Aug. 23, 2004.

(51) Int. Cl.
*A01H 5/00* (2006.01)

(52) U.S. Cl. ..... Plt./318

(58) Field of Classification Search ..... Plt./318
See application file for complete search history.

*Primary Examiner*—Anne Marie Grunberg
*Assistant Examiner*—Georgia Helmer
(74) *Attorney, Agent, or Firm*—The Webb Law Firm

(57) ABSTRACT

A new and distinct cultivar of New Guinea *Impatiens* plant named 'Applause White', characterized by its compact, mounded plant habit; freely branching growth habit; freely flowering habit with flowers polished above the foliage; large white-colored flowers; and tolerance to full sun conditions and low and high temperatures.

1 Drawing Sheet

Botanical classification: *Impatiens hawkeri.*
Varietal denomination: 'Applause White'.

BACKGROUND OF INVENTION

The present invention comprises a new and distinct cultivar of *Impatiens hawkeri,* known by the cultivar name 'Applause White'. The new variety is a product of a planned breeding program conducted in Lompoc, Calif. The purpose of the breeding program was to create earlier flowering cultivars with larger flower size, white flowers, and a compact, mounded plant habit. The new variety originated from a cross-pollination during the fall of 1998 of a proprietary selection of *Impatiens hawkeri* identified as code number 98-563-2, not patented, as the female seed parent with a proprietary selection of *Impatiens hawkeri,* identified as code number 97-253-4, not patented, as the male pollen parent. Comparisons between the new variety and its parents cannot be made, as the parental varieties no longer exist. The cultivar 'Applause White' was discovered and selected as a flowering plant within the progeny of the stated cross in a controlled environment in Lompoc, Calif. Asexual reproduction of the new cultivar by terminal cuttings has shown that the unique features of the new variety are stable and reproduced true to type in successive propagations.

The following traits have been repeatedly observed and are determined to be the unique characteristics of 'Applause White'. Characteristics that distinguish 'Applause White' as a new and distinct cultivar from others known to the breeder include:

1) Compact, mounded habit;
2) Freely branching;
3) Large flowers, approximately 70 mm in diameter;
4) Tolerates high temperatures and full sun conditions;

5) Tolerates cool night temperatures to 5° C.,
6) Rounded flowers are carried over the foliage canopy; and
7) Early to flower, finishing 7 weeks in a 10 cm pot.

Plants of the new variety can be compared to plants of the *Impatiens* cultivar 'Ovation Bright White', disclosed in U.S. Plant Pat. No. 12,959. In side-by-side comparisons conducted by the Inventor in Lompoc, Calif., plants of the new variety differed from plants of the cultivar 'Ovation Bright White' in the following characteristics:

1) Flowers of the new variety were larger than the flowers of 'Ovation Bright White';
2) Plants of the new variety had a mounded habit and a height of 12 to 15 cm, whereas the plants of 'Ovation Bright White' had a semi-upright habit and a height of 22 to 25 cm;
3) Plants of the new variety had a stem color of 146C, whereas plants of 'Ovation Bright White' had a stem color of 146C with a cast around the nodes of 184B;
4) Plants of the new variety finished faster than plants of 'Ovation Bright White'; and
5) Leaf width measurements of the new variety were wider than the leaf width measurements of 'Ovation Bright White'.

BRIEF DESCRIPTION OF THE DRAWING

The accompanying colored photographic drawing illustrates the new variety with the colors being as nearly true as is possible to obtain in colored illustrations of this type.

DESCRIPTION OF THE PLANT

Figure 1:
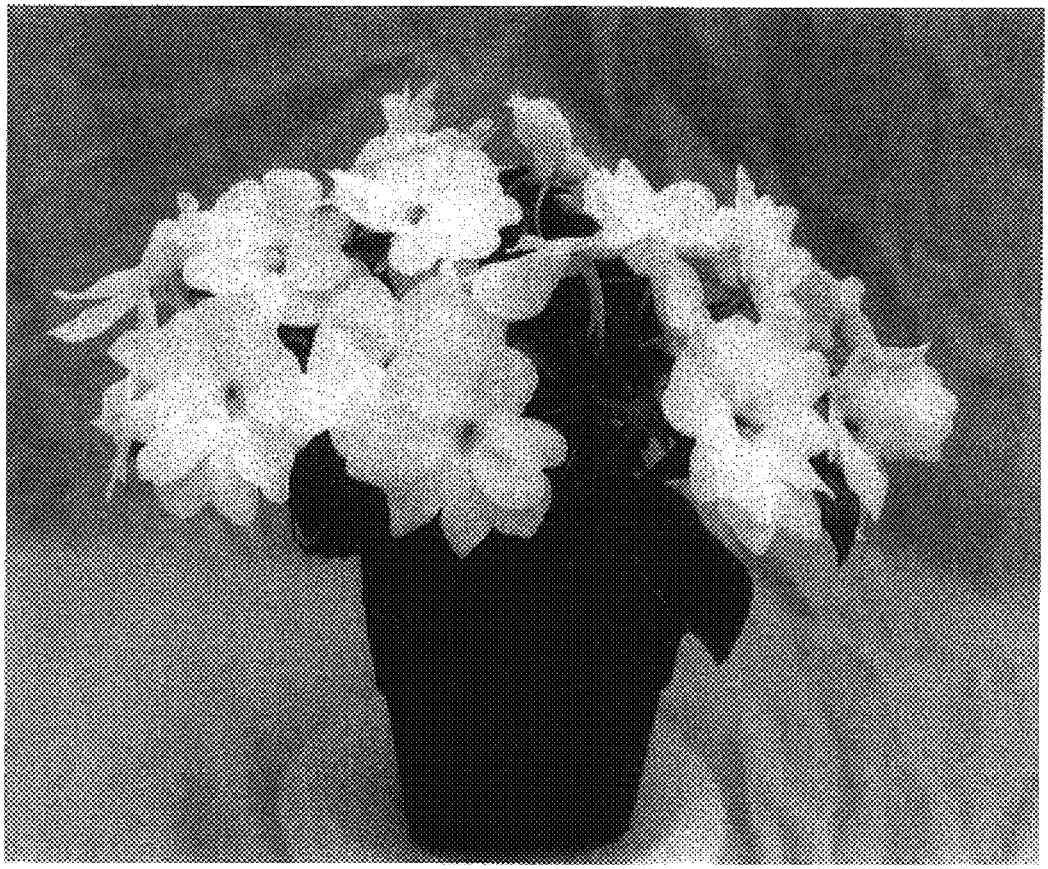

The cultivar 'Applause White' has not been observed under all possible environmental conditions. The phenotype may vary somewhat with variations in environment such as temperature, day length and light intensity. However, there is no variance in genotype.

In the following description, color references are made to The Royal Horticultural Society Colour Chart, 1995 Edition, except where general terms of ordinary dictionary significance are used. Plants were grown under commercial practice during the late winter through early spring of 2003 in Lompoc, Calif., in a corrugated polycarbonate-covered greenhouse with 30% shade covering. During the production of the plants, day temperatures ranged from 21 to 24° C.; night temperatures ranged from 16 to 18° C. and light levels ranged from 3000 to 4000 foot candles of light. Plants used in the following description were grown in 10 cm containers for about seven to nine weeks after planting rooted cuttings.

Propagation:

*Type cutting.*—Terminal cuttings.

*Time to initiate roots.*—Summer: About 10 days at 21° C. Winter: About 12 days at 21° C.

*Time to produce a rooted cutting.*—Summer: About 21 days at 21° C. Winter: About 21 days at 21° C.

*Root description.*—Fibrous, white in color.

*Root habit.*—Freely branching, dense.

Plant description:

*General appearance.*—Mounded plant habit; numerous flowers positioned above the foliage.

*Plant height at flowering.*—12 to 15 cm.

*Plant width* (*spread*).—20 to 25 cm.

*Growth and branching habit.*—Freely branching habit; dense and full plant habit; typically 10 or more lateral branches develop per plant. Pinching (removal of terminal apex) is usually not required. Vigorous growth habit.

*Lateral branch description.*—Length: About 12 to 15 cm. Diameter: About 5 to 6 mm. Internode length: About 3 to 4 cm. Color: 146C.

*Foliage description.*—Arrangement: Alternate or whorled; simple. Length: About 8 to 9 cm. Width: About 3 to 3.5 cm. Shape: Lanceolate. Apex: Acuminate. Base: Acute. Margin: Finely serrated with fine ciliate. Texture, upper and lower surfaces: Glabrous. Venation pattern: Pinnate. Color: Developing leaves, upper surface: 146A. Developing leaves, lower surface: 148B. Fully expanded leaves, upper surface: 147A. Fully expanded leaves, lower surface: 148B. Venation, upper surface: 147B. Venation, lower surface: 146B. Petiole length: About 12 to 15 mm. Petiole diameter: About 4 mm. Petiole color: 60A.

Flower description:

*Flower type and habit.*—Single, large, rounded, flat, and white-colored flowers. Freely flowering, usually about one flower per leaf axil. Flowers positioned above the foliage and typically face upward or outward. Flowers last about two weeks on the plant depending on environmental conditions. Petals self-cleaning. Flowers not fragrant.

*Flowering season.*—Year-round under greenhouse conditions. In the garden, flowering from spring until fall. Flowering indeterminate and continuous.

*Flower diameter.*—About 7 cm.

*Flower buds.*—Length: About 2 cm. Width: About 1.2 cm. Shape: Ellipsoidal. Color (just before opening): 157C.

*Petals.*—Quantity: Five. Length: About 3 to 3.5 cm. Width: About 3.5 to 4 cm. Shape: Cordate. Apex: Rounded with moderate indentations. Base: Rounded to acute. Margin: Entire. Texture, upper and lower surfaces: Glabrous, satiny. Color: When opening, upper surface: 155C. When opening, lower surface: 155C. Fully opened, upper surface: 155D. Fully opened, lower surface: 155C.

*Spur.*—Length: About 5 cm. Color: 146D.

*Peduncles.*—Length: About 3.5 cm. Angle: About 45° from vertical. Strength: Strong. Texture: Smooth, glabrous. Color: 146D.

*Reproductive organs.*—Androecium: Stamen description: Five fused at anthers, filaments free, hooded. Anther length: About 6 mm. Anther shape: Obovate. Anther color: 155C, near tip, 9C. Pollen amount: Abundant. Pollen color: 155C. Gynoecium: Pistil number: One pistil; five-parted. Pistil length: About 6 mm. Stigma color: Off-white. Style color: Off-white. Ovary color: 146C.

Fruit/seed development: Fruit and seed development has not been observed.

Disease/pest resistance: Plants of the new *Impatiens* have not been observed to be resistant to pathogens and pests common to *Impatiens*.

Temperature tolerance: In outdoor nursery trials in Connellsville, Pa., plants of the new variety have been observed to be tolerant to full sun conditions and high temperatures (32 to 38° C.) during the summer. In outdoor nursery trials in Lompoc, Calif., plants of the new variety have been observed to be tolerant to low night temperatures from about 5 to 10° C.

I claim:

1. A new and distinct variety of *Impatiens* plant named 'Applause White' as herein described and illustrated.

* * * * *